United States Patent
Kwon et al.

[11] Patent Number: 6,151,108
[45] Date of Patent: Nov. 21, 2000

[54] ON-LINE MEASUREMENT OF CONTAMINANT LEVEL IN LUBRICATING OIL

[75] Inventors: Oh Kwan Kwon; Ho Sung Kong; Hung Gu Han; Eui-Sung Yoon, all of Seoul, Rep. of Korea; N. K. Myshkin, Gomel, Belarus; L. V. Markova, Gomel, Belarus; M. S. Semeniouk, Gomel, Belarus

[73] Assignee: Korea Institute of Science and Technology, Seoul, Rep. of Korea

[21] Appl. No.: 09/386,168

[22] Filed: Aug. 31, 1999

[30] Foreign Application Priority Data

Aug. 31, 1998 [KR] Rep. of Korea ............. 98-35577

[51] Int. Cl.$^7$ .................................................... G01N 33/28
[52] U.S. Cl. ...................................... 356/70; 356/338
[58] Field of Search .......................... 356/70, 337, 338, 356/339, 135, 136

[56] References Cited

U.S. PATENT DOCUMENTS

| 4,570,069 | 2/1986 | Gager . |
| 4,699,509 | 10/1987 | Kamiya et al. . |
| 4,848,905 | 7/1989 | Lino ........................................ 356/338 |
| 5,739,916 | 4/1998 | Englehaupt . |
| 5,790,246 | 8/1998 | Kuhnell et al. . |

FOREIGN PATENT DOCUMENTS

| 0 635 714 | 1/1995 | European Pat. Off. . |
| 57098842 | 6/1982 | Japan . |

Primary Examiner—Frank G. Font
Assistant Examiner—Roy M. Punnoose
Attorney, Agent, or Firm—Oblon, Spivak, McClelland, Maier & Neustadt, P.C.

[57] ABSTRACT

A measurement apparatus determines contaminant level of oil by qualitatively measuring the light intensity after the light has transmitted through an oil sample. The apparatus comprises light emitting means for generating light to be provided to the oil sample, a container for storing the oil sample, the container being displaced from the light emitting means by a predetermined distance, light receiving means for detecting the intensity of light transmitted through the oil sample, the receiving means being displaced from the container by a predetermined distance, first light conveyance means for conveying the light generated by the light emitting means as coherent light to the oil sample, second light conveyance means for conveying the light transmitted through the oil sample to the light receiving means, wherein the characteristics of the light emitting means and the light receiving means are controlled so that they do not vary depending on the temperature of the oil sample.

8 Claims, 5 Drawing Sheets

ON-LINE MEASUREMENT OF CONTAMINANT LEVEL IN LUBRICATING OIL

BACKGROUND OF THE INVENTION

1. Field of the Invention

The present invention relates to an on-line measurement of the amount of contaminant particles in lubricating oil, more particularly, to an apparatus which measures the amount of paramagnetic and non-magnetic contaminant particles in lubricating oil.

2. Description of the Prior Art

Due to the recent epochal development of technology in many industrial fields, technologies for preventive maintenance and monitoring the optimum conditions of machinery are widely needed to prevent an unexpected failure and an accident resulting from such failure in a system ranging from a vehicle to a large plant such as a power plant, an iron mill or a petrochemical plant.

Condition diagnosis technologies which has been put to practical use up to date can be classified based on a measurement method used therein into: a method for measuring variables used for system operation, e.g., temperature, pressure, and velocity; a method for measuring physical or chemical changes of mechanical parts or lubricating oil; a method for measuring energy loss due to friction or loss of material from abrasion. The technologies can also be classified based on a measurement period into an off-line method by which periodical checkup is made and an on-line method by which real time checkup is possible.

The present invention is related to a system for qualitatively measuring contamination level in lubricating oil. These kinds of technologies are the most important among various condition diagnosis technologies because by using them one can observe and detect the degree of damage, if any, of parts in a machine under operation without disassembling the machine at any time or in a continuous manner.

A condition diagnosis technique through a measurement of contamination level is to determine the health of a mechanical system, i.e., whether the system is damaged or in a normal condition, by measuring and analyzing the quantity of contaminant particles in lubricating oil used in the system which are produced by the wear in the system or provided from the exterior of the system. This technique is also called "machine health diagnosis" because it is similar to the technique for monitoring the health condition of a human body by qualitatively measuring the number of white or red blood cells.

In the condition diagnosis technologies using the measurement of the contaminant level, qualitative and/or quantitative measurements are made. As the quantitative measurement, the amount of wear debris is measured which is produced from machine elements as they are used. As the qualitative measurement, constituents of the wear debris are analyzed, changes of the particle size of the wear debris are measured, it is determined whether the contaminant has been introduced from the exterior of the system, and the degree of corrosion or oxidation of the machine parts is measured. Through these measurements and analyses, it is first determined whether the mechanical system is in a proper condition. Moreover, the analysis of changing characteristics of the wear debris can give early warning of impending failure. Also, one can understand major causes of the wear in the system from prolonged analysis of the wear characteristics. Result of such analysis can also be used in redesigning an improved system.

There have been many condition monitoring technologies by which one can qualitatively measure the contamination level in lubricating oil. Spectroscopy and a particle counter are examples of off-line condition monitoring techniques where oil samples are analyzed in a laboratory.

The spectroscopic apparatus, which determines the constituents of contaminant and their amount in lubricating oil, is currently used, e.g., to diagnose the condition of an airplane engine. Although it can precisely measure the contaminant level, it cannot give information on the size of contaminant particles and can only measure and analyze particles ranging in size from 1 to 20 $\mu$m.

The particle counter is an apparatus for precisely measuring the size of contaminant particles, the distribution of the size, and total contaminant level. It has its own drawbacks in that it cannot be used for oil with high contaminant level and that it cannot give any information on the constituents of the contaminant particles.

Other condition monitoring techniques include a ferrographic apparatus disclosed in U.S. Pat. No. 4,187,170, a Rotary Particle Depositor (RPD) disclosed in U.K. Pat. No. 8,121,183 and a Particle Quantifier (PQ). In the ferrography and the RPD, contaminant particles are fixed to a surface of a transparent glass according to their sizes and the fixed particles are magnified and visualized by using an optical or electric microscope, so that the size, shape and color of the particles are analyzed. By analyzing the characteristics of the contaminant particles, we can identify the reason why the contaminant has been introduced to the oil and get information on the current condition of the system. However, in these techniques, the analysis results can be varied depending on the subjective view of the analyzer.

The above off-line methods for measuring and analyzing the contaminant level of the lubricating oil in a laboratory are inconvenient in that oil samples should be taken and carried to the laboratory periodically. During such sampling process, errors may occur. Moreover, by these off-line methods, one cannot detect a sudden failure of machinery and therefore an accident resulting from it cannot be prevented.

Examples of conventional apparatus for real-time measuring of contaminant level are a Quantitative Debris Monitor (QDM), a Magnetic Chip Detector and a Fluid Condition Monitor (FCM).

The QDM is a device for measuring contaminant level by magnetically inducing contaminant particles, making the induced particles collide with a surface of a sensor, and then observing voltage pulses resulting from such collision. Particles that can be measured by the QDM is limited to those over 100 $\mu$m. In addition, since the surface of the sensor is prone to damage, the sensor should be frequently replaced.

In the magnetic chip detector, magnetic material is inserted in the lubricating oil so that paramagnetic contaminant particles are adhered to surfaces of the magnetic material. Then, the magnetic material is periodically analyzed by, for example, human eyes. Its merit is that it can be easily used in an industrial field. However, the paramagnetic particles that can be adhered to the surface of the magnetic material are limited to those over 100 μm and, moreover, it cannot provide information on nonmagnetic contaminant particles.

Korean Patent No. 150054 is directed to "Method and apparatus for on-line monitoring of wear debris in lubricating oil." In summary, it discloses measuring the quantity of particles in the oil by measuring the amount of light intercepted by the particles when the light passes through the oil. It also discloses a method for separately measuring contaminant level due to paramagnetic particles by measuring the amount of light after selectively locating permanent magnets above the oil container and thereby isolating paramagnetic particles in the oil from the light passages. The above method has several drawbacks. First, to induce the minute particles distributed in the oil towards the magnet against the resistance of the oil, very strong magnet should be used, thus making the apparatus bulky. Second, it is highly probable that the oil which is being used in a field contains air bubbles. Therefore, if such oil is directly used for contaminant measurement and light is used as a measuring medium, air bubbles can be misidentified as contaminant particles so that the measured contaminant level may be higher than a real value. Moreover, the above patent simply mentions "on-line" measurement in its title but does not specifically disclose how the contaminant is measured on-line. Third, although the light-attenuating effect of the oil may vary depending on the viscosity of the oil, only the light-blocking effect of opaque contaminant particles is considered with no regard to the viscosity. Therefore, in an on-line measurement system, in order not to be affected by the change of viscosity, a device for maintaining constant viscosity is necessary, or alternatively, the amount of light should be adjusted depending on the temperature.

From the above, we can identify a couple of advantageous features of an online contaminant measurement system. First, it is preferable to analyze the contaminant particles qualitatively as well as quantitatively. Major elements in machinery are made of both paramagnetic material such as iron and non-magnetic material such as aluminum and copper. Therefore, by separately measuring the amount of wear debris constituting both material, we may detect machine parts where severe wear occurs.

Second, to use an on-line measurement system in a field for a long time, the cost of maintenance and repair should be minimized. In conventional measurement systems, filters or electromagnetic coated films are generally used. In a system where difference of pressure or liquid flow before and after the filter is measured, contaminant particles remaining on the surface of the filter should be removed by letting the liquid flow reversely after the measurement. However, it is difficult to know whether the filter is washed clean and the filter should be replaced after it is used for a certain amount of time. The electromagnetic coated film should also be replaced since it is damaged by the measurement.

SUMMARY OF THE INVENTION

It is an object of the present invention to provide a system for measuring the amount of contaminant particles on a real time basis.

It is another object of the present invention to provide a measurement system for analyzing the contaminant particles qualitatively as well as quantitatively.

It is yet another object of the present invention to provide a measurement system whose maintenance and repair costs are low.

In accordance with the present invention, there is provided an apparatus for determining contaminant level of oil by qualitatively measuring the light intensity after the light has transmitted through an oil sample, said apparatus comprising:

light emitting means for generating light which is to be provided to the oil sample;

a container for storing the oil sample, said container being displaced from the light emitting means by a predetermined distance;

light receiving means for detecting the intensity of light transmitted through the oil sample, said receiving means being displaced from the container by a predetermined distance;

first light conveyance means for conveying the light generated at the light emitting means as coherent light to the oil sample; and second light conveyance means for conveying the light transmitted through the oil sample to the light receiving means, wherein the characteristic of the light emitting means and the light receiving means are controlled so that they do not vary depending on the temperature of the oil sample.

BRIEF DESCRIPTION OF THE DRAWINGS

The above and other objects and features of the present invention will become apparent from the following descriptions of the preferred embodiments taken in conjunction with the accompanying drawings, in which.

DETAILED DESCRIPTION OF THE INVENTION

A system for measuring contaminant level in accordance with the present invention may be used to measure the amount of contaminant particles in any oil including lubricating oil. An embodiment for measuring contamination level of lubricating oil will be described.

The measurement system of the present invention can measure the amount of paramagnetic and non-magnetic contaminant particles separately. It determines the level of contaminant including wear debris produced in the oil and impurities introduced from outside by measuring the change of light transmitted through the oil.

In the present invention, a predetermined amount of oil is sampled and the oil sample is put to a cylindrical container. Then, light is transmitted through the container by using light sensors, where a infrared ("IR") light emitting diode ("LED") may be used as a light emitter and a photodiode may be used as a light receptor. By measuring the change of optical density, i.e., the amount of light transmitted through oil sample in the container, the contamination level in the oil can be quantitatively determined. Generally, wear debris generated in the lubricating oil consists of paramagnetic or ferromagnetic particles. Therefore, magnetic properties of these wear debris are different from those of the impurities externally provided to the oil. To utilize this difference, strong magnetic field is applied around the cylindrical oil container in the present invention. When the magnetic field is applied to the oil sample, lines of magnetic force are formed vertically in the container and magnetic particles are arranged along the magnetic lines. Therefore, when the magnetic field is applied, the intensities of light transmitted through the oil increase. By measuring the optical density before and after the magnetic field is applied, the ratio between magnetic wear debris and non-magnetic impurities can be determined.

Optical lenses are used to make the light passing through the container coherent. To compensate for the temperature characteristic of the diodes, the light emitted from the LED is measured and, by feedback control, a constant amount of light is directed to the oil sample. In addition, optical fiber is used to make the characteristic of the light emitting and receiving diodes independent of temperature and to separate an amplifier including the light emitting and recepting diodes from a sensing device including the oil container.

Figure 1:
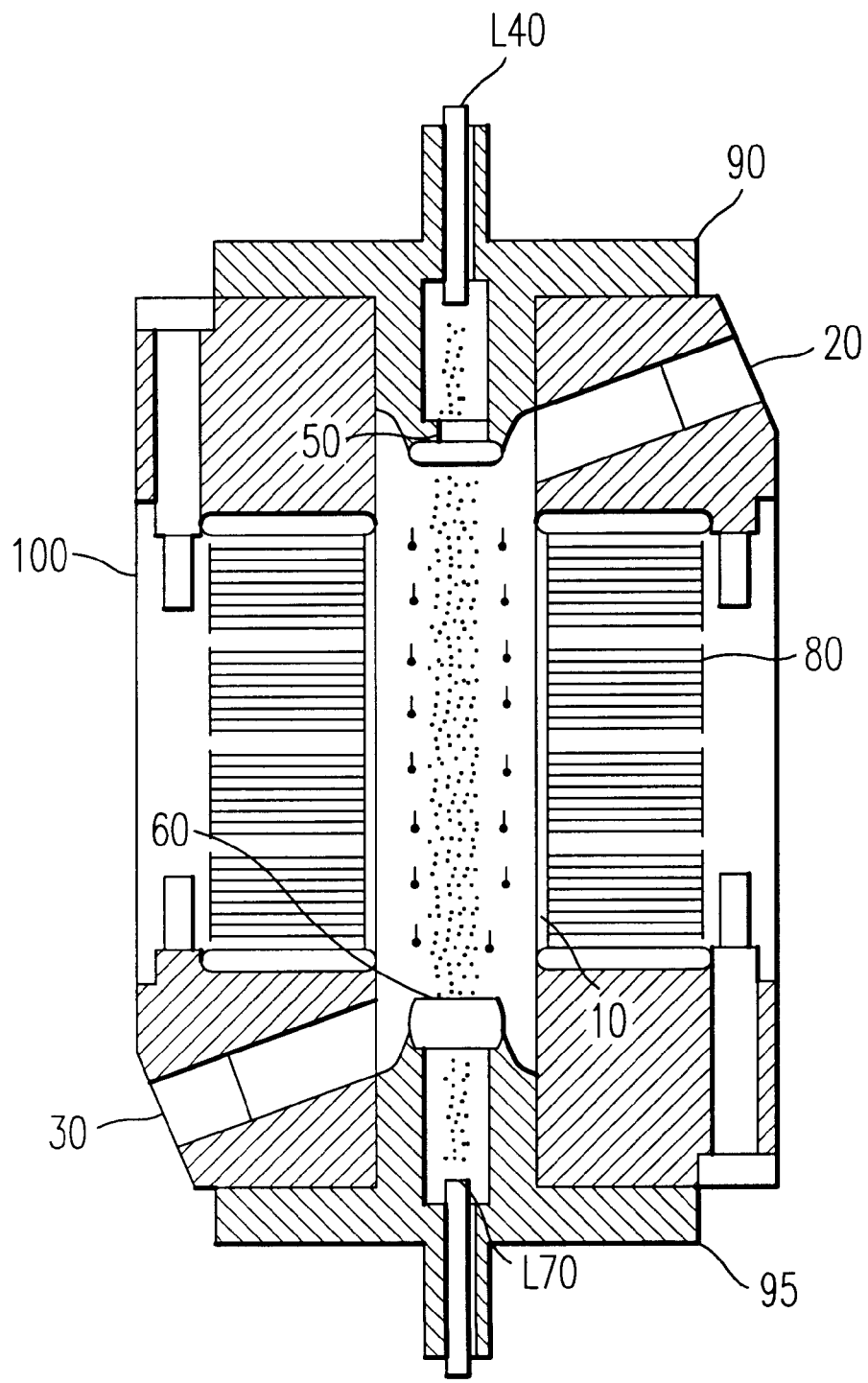
FIG. 1 shows a sensing device for measuring contaminant level in accordance with the present invention.

FIG. 1 illustrates a sensing device 310 for measuring contaminant level in accordance with the present invention. The device 310 includes a cylindrical container 10 where the oil sample is provided and circulated for on-line measurement through an inlet 20 and an outlet 30. The device 310 also includes an optical fiber L40 for delivering IR light generated by from an infrared ("IR") LED (not shown), an light-inputting optical lens 50 which converts the light delivered by the optical fiber to a coherent light and directing it into the oil sample, an light-receiving optical lens 60 for collecting the light attenuated while transmitted through the oil sample and focusing the collected light to another optical fiber L70, the optical fiber L70 which deliver the collected light to a photodiode (not shown), a solenoid coil 80 for applying magnetic field to the oil sample in the container 10, members 90, 95 for fixing the optical fibers L40, L70 and the optical lenses 50, 60, and a case 100 for protecting the interior of the sensing device 310.

Figure 4:
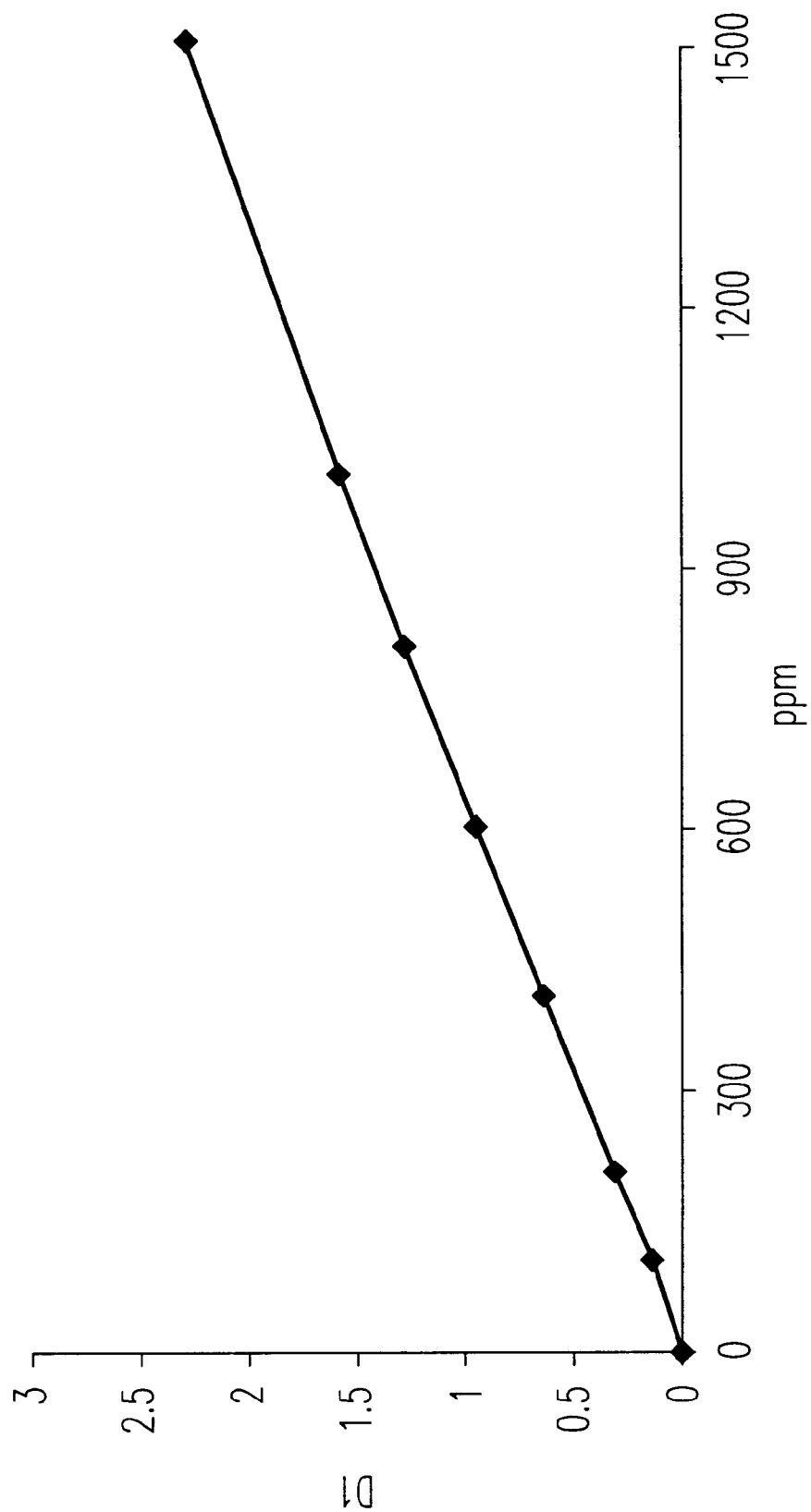
FIG. 4 shows values of optical density $D_1$ of a lubricating oil measured by the sensing device of the present invention.
Figure 5:
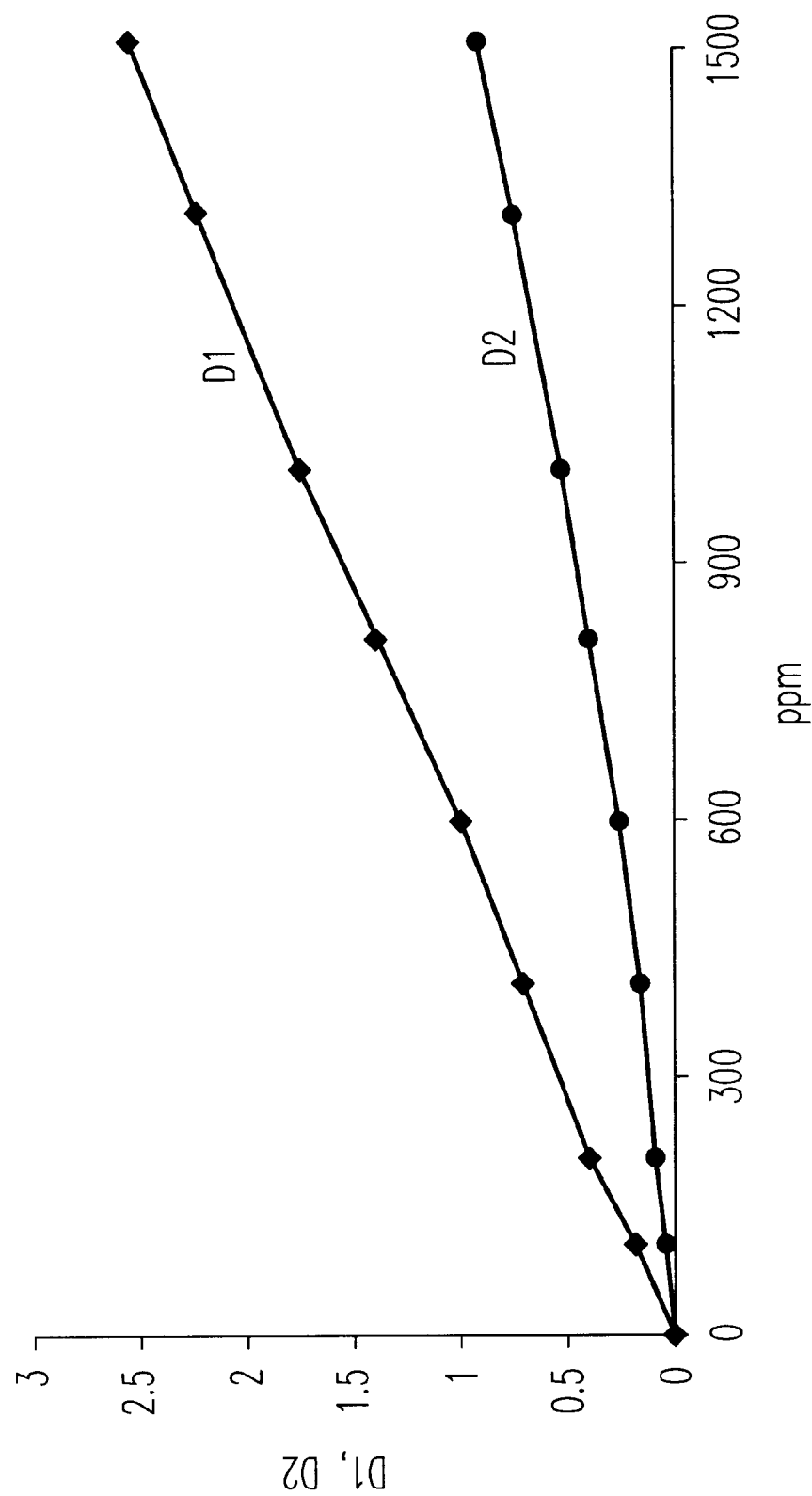
FIG. 5 shows values of optical density $D_1$ and $D_2$ of a lubricating oil measured by the sensing device of the present invention.

Generally, intensity of light transmitted through a medium is represented as follows:

$$I_1 = I_0 e^{-\alpha x} \quad \text{Eq. (1)}$$

where $I_1$ is the intensity of light transmitted through the medium, $I_0$ is the intensity of incident light, x is the length through which the light travels, σ is an attenuating factor which is proportionally related to the concentration of contaminant particles in the medium. Therefore, logarithm of the light intensity transmitted through the medium is proportional to the concentration of contaminant particles, By using the above relationship, change of optical density of the oil due to the contaminant particles depends upon the contamination level and the strength of the magnetic field and is represented as follows:

$$D_1 = \ln \frac{J_1}{J_2} \quad \text{Eq. (2)}$$

$$D_2 = \ln \frac{J_3}{J_2} \quad \text{Eq. (3)}$$

$$D_3 = \ln \frac{J_3}{J_4} \quad \text{Eq. (4)}$$

where $J_1$ is the optical density of unused oil, $J_2$ is the optical density of used oil, $J_3$ is the optical density of the used oil after the magnetic field is applied, $J_4$ is the optical density of the used oil after the magnetic field is removed, Thus, the change of optical density, $D_1$, is determined by measuring the optical densities $J_1$ and $J_2$ of the unused and used oil, respectively. Amount of contaminant particles in the oil corresponding to the determined $D_1$ value is obtained by referring a graph (as shown in FIGS. 4 and 5) representing values of $D_1$ versus contaminant level which are experimentally predetermined by measuring $D_1$ values for various standard contaminant levels.

When a magnetic field is applied to the container 10, paramagnetic contaminant particles are arranged along the magnetic lines so that the optical density changes from $J_2$ to $J_3$. From Eq. (3), relative contaminant level due to the paramagnetic particles alone can be determined. The amount of paramagnetic particles may be determined by referring the result of an experiment conducted before the measurement. After the magnetic field is removed, small particles among those arranged along the magnetic lines are dispersed back into the oil. As a result, the optical density is decreased a little to $J_4$. Thus, $J_4$ may be used to determine the contaminant level due to the small particles.

Figure 2:
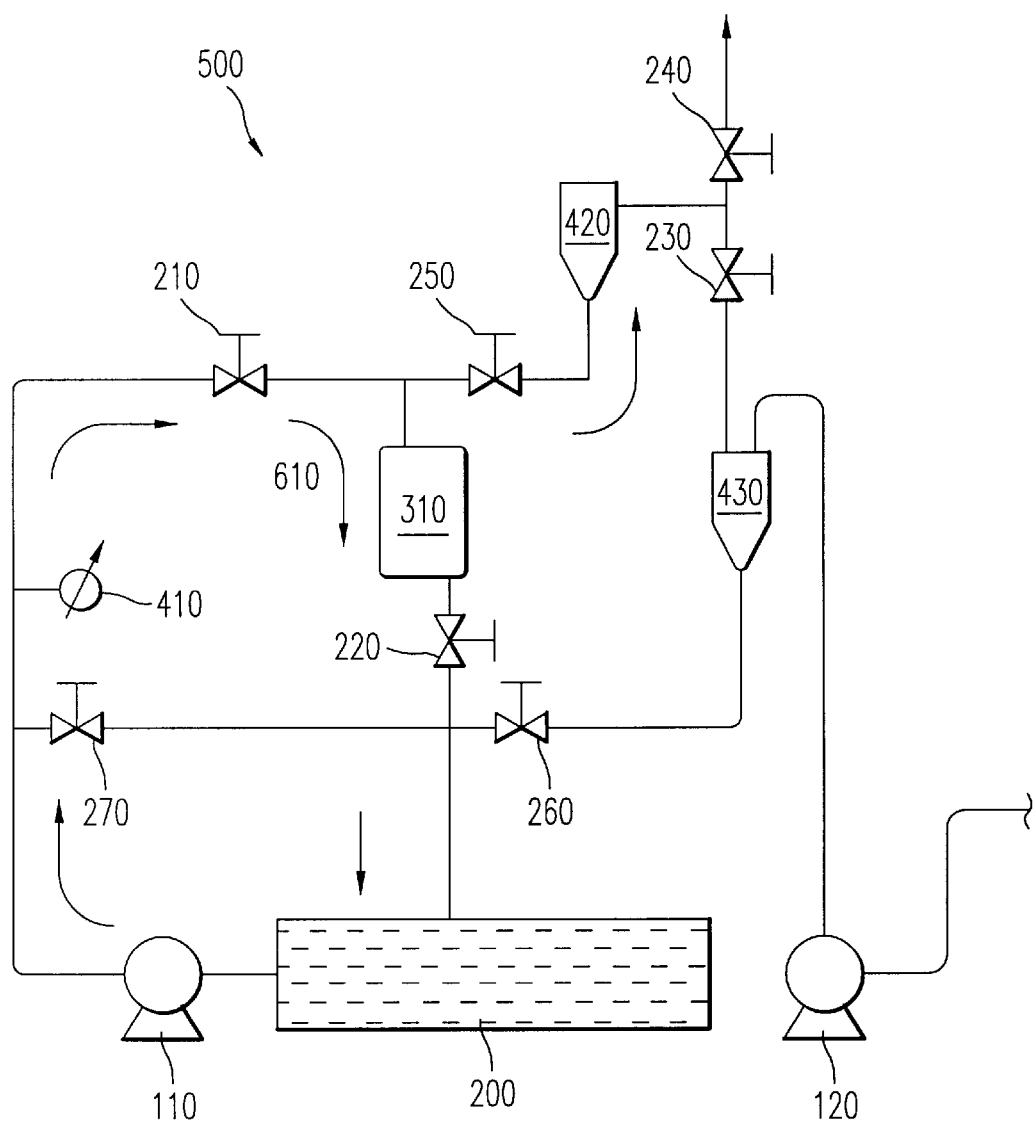
FIG. 2 shows an oil circulation system which includes the sensing device shown in FIG. 1, parts for providing oil to the sensing device, and a vacuuming device for removing bubbles from the oil.

FIG. 2 shows an oil circulation system 500 which includes the sensing device 310 in accordance with the present invention, parts for providing the oil from an oil tank 200 to the sensing device 310, and parts for vacuuming which remove bubbles from the oil. A trochoid pump 110, functioning as an oil circulating pump, provides he oil from the oil tank 200 to the sensing device 310 under the control of an input air pressure valve 210 and an output air pressure valve 220. A pressure switch 410 is provided to ensure safety by controlling a solenoid valve 270 with a signal from the switch 410 against a case where oil pressure in tube exceeds a predetermined value. The parts for vacuuming include a solenoid valve 230 for applying the vacuum from a vacuuming pump 120, a solenoid valve 240 for returning to the ambient air state from the vacuum state, an air pressure valve 250 for controlling the circulation of the oil and the vacuum, a chamber 420 for preventing the oil from flowing backwards to the vacuum line during the vacuum state and also acting as a buffer to remove the air bubbles from the oil, an oil trap 430 for collecting vaporized oil and backward-flowing oil and draining out the collected oil.

The circulation system 500 depicted in FIG. 2 can be operated in two ways. It can be used both for manual measurement of the contamination level or real-time measurement. The procedure for manual measurement is as follows:

1) Apply power to the system.
2) Operate the oil circulating pump 110.
3) Stop the oil circulating pump 110 after the oil has been sufficiently circulated. Operate the vacuuming pump 120 to remove bubbles from the oil.
4) Put the air in the oil in the vacuum state and the ambient air state alternately until the air bubbles are completely removed.
5) Stop the vacuuming pump 120 when the bubbles are removed. Return to the ambient air state and measure the optical density $J_2$ of the used oil.
6) Apply power to the electromagnetic coil 80 of the sensing device 310. 60 seconds after the power is applied, measure optical density $J_3$ of the used oil. Turn off the power and, after 60 seconds, measure optical density $J_4$ of the used oil.
7) Open the valves to drain out the oil sample from the container 10.
8) From the measured values $J_2$, $J_3$, and $J_4$, determine a total contaminant level and contaminant levels due to paramagnetic and non-magnetic particles by referring contaminant level values predetermined by experiments.

The circulation system 500 in accordance with the present invention can also be used for real-time measurement of contaminant level of lubricating oil in industrial fields. For this purpose, the air pressure and solenoid valves are automatized by using a programmable logic controller ("PLC") so that the oil can be sampled automatically. Moreover, an independent measurement system is provided where the measurement results are analyzed in a computer which is connected to an external communication network for data transmission.

Figure 3:
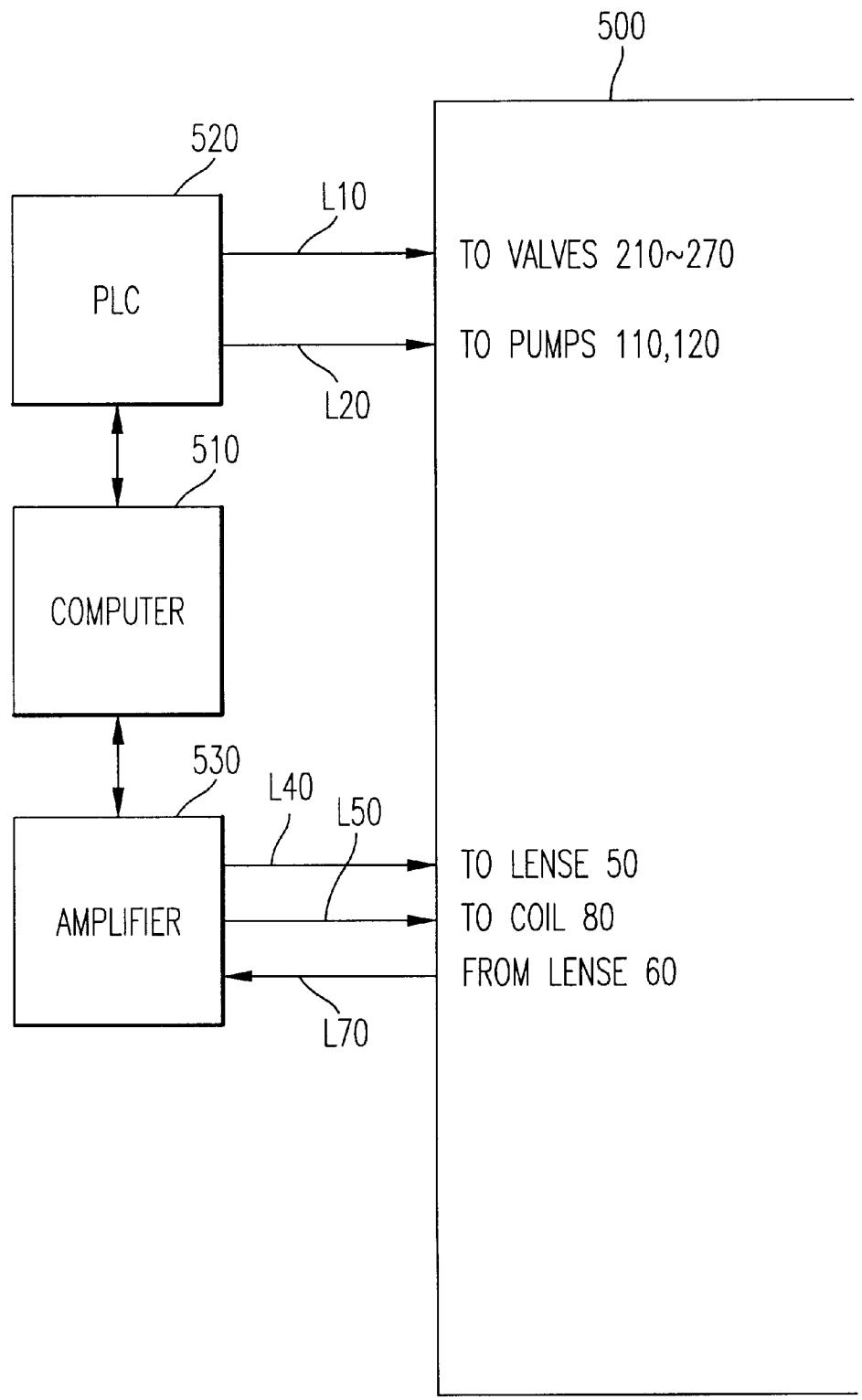
FIG. 3 shows a measurement system of the present invention.

FIG. 3 shows a real-time measurement system including the circulation system 500 shown in FIG. 2, a PLC for controlling the solenoid and air pressure valves and pumps, a computer 520 for controlling the circulation system and processing, storing and displaying data obtained from the measurement and an amplifier 530 for generating light to be provided to the sensing device 310, receiving light collected from the sensing device 310, and providing a magnetic field to the oil.

In response to instructions from the computer 510, the PLC 520 operates to control the pumps 110, 120 and valves 210 to 270. Light is generated at an light emitting device, e.g., infrared LED, in the amplifier 530 which is displaced from the sensing device 310 and then conveyed through the optical fiber L40 to the sensing device 310. Light transmitted through the oil is provided via the optical fiber L70 back to an light recepting device, e.g., photodiode, in the amplifier 530. In this system, the measuring procedure explained above is repeated at regular intervals. Measurement results are converted to digital values by using an analog/digital converter (not shown). The digitized measurement values are inputted to the computer 510, stored therein and displayed on the monitor of the computer.

FIG. 4 depicts values of optical density change $D_1$ of lubricating oil measured by the sensing device of the present invention as the contamination level of the oil is changed by using ACMTD particles. The concentration of the contaminant particles in the oil is set to 100, 200, 400, 600, 800, 1000, and 1500 ppm. It is observed that the optical density increases linearly as the contamination level (in ppm) increases. The inclination of the linear increase is 0.00168, the regression coefficient is 0.995, and the standard deviation is 0.11652. Thus, the observed relationship between the optical density and the contamination level is nearly linear.

FIG. 5 depicts values of values optical density change $D_1$ and $D_2$ of lubricating oil measured by the sensing apparatus of the present invention using carbonyl iron powder as the contaminant. The concentration of the contaminant particles in the oil is set to 100, 200, 400, 600, 1000, 1300 and 1500 ppm. It is observed that both $D_1$ and $D_2$ increase linearly as the contamination level (in ppm) increases. For $D_1$, the inclination of the linear increase is 0.00168, the regression coefficient is 0.999, and the standard deviation is 0.02217 and for $D_2$, the inclination of the linear increase is 0.000577, the regression coefficient is 0.992, and the standard deviation is 0.04281. Thus, the observed relationship between $D_1$, or $D_2$ and the contamination level is nearly linear.

By using the on-line measurement system of contaminant level in accordance with the present invention, the contaminant level in lubricating oil can be qualitatively measured on a real-time basis. Moreover, since the contaminant particles can be qualitatively analyzed, parts of a mechanical system where severe wear occurs can be identified.

While the present invention has been described with respect to the particular embodiments, it will be apparent to those skilled in the art that various changes and modifications may be made without departing from the spirit and scope of the invention as defined in the following claims.

What is claimed is:

1. An apparatus for determining a contaminant level of oil by qualitatively measuring the light intensity after the light has transmitted through an oil sample, said apparatus comprising:

light emitting means for generating light to be provided to the oil sample;

a container for storing the oil sample, said container being displaced from the light emitting means by a predetermined distance;

light receiving means for detecting the intensity of light transmitted through the oil sample, said receiving means being displaced from the container by a predetermined distance;

first light conveyance means for conveying the light generated by the light emitting means as coherent light to the oil sample; and second light conveyance means for conveying the light transmitted through the oil sample to the light receiving means, wherein the characteristics of the light emitting means and the light receiving means are controlled so that they do not vary depending on the temperature of the oil sample.

2. An apparatus for measuring a contaminant level in accordance with claim 1, wherein said fist light conveyance means includes:

a first optical fiber connected to the light emitting means for conveying the light from the light emitting means; and a first optic lens for directing the light conveyed through the first optical fiber as the coherent light into the container.

3. An apparatus for measuring a contaminant level in accordance with claim 1, wherein said second light conveyance means includes:

a second optic lens for collecting the light transmitted through the oil sample; and a second optic fiber for conveying the collected light to the light receiving means.

4. An apparatus for measuring a contaminant level in accordance with claim 1, wherein the light emitting means includes an infrared light emitting diode ("IR LED") and the light receiving means includes a photodiode.

5. An apparatus for measuring a contaminant level in accordance with claim 4, wherein said IR LED emits light whose wavelength ranges from 650 nm to 1050 nm.

6. An apparatus for measuring a contaminant level in accordance with claim 1, said apparatus further comprising means for removing air bubbles from the oil sample.

7. An apparatus for measuring a contaminant level in accordance with claim 1, said apparatus further comprising a solenoid arranged around the container for selectively applying a strong magnetic field to the oil sample, wherein, in case the magnetic field is applied, vertical magnetic lines are formed in the container, and contaminant particles in the oil sample are aligned along the magnetic lines so that the relative ratio of paramagnetic particles and non-magnetic particles among the contaminant particles is determined by measuring the intensity of light transmitted through the oil sample before and after the magnetic field is applied.

8. An apparatus for measuring a contaminant level in accordance with claim 1 which further comprises:

means for providing the oil sample to the container;

means for removing air bubbles from the container, said providing means and removing means including a solenoid and air pressure valves;

a programmable logic controller for controlling the solenoid and air pressure valves;

processor means for processing data obtained from the qualitative measurement; and means for connecting the processor means with an external communication network.

* * * * *

UNITED STATES PATENT AND TRADEMARK OFFICE
CERTIFICATE OF CORRECTION

PATENT NO.   : 6,151,108
DATED        : November 21, 2000
INVENTOR(S)  : Kwon et al.

It is certified that error appears in the above-identified patent and that said Letters Patent is hereby corrected as shown below:

<u>Title page,</u>
Item [73], the Assignee information is incorrect.
Item [73] should read as follows:

--- [73] Assignee:    O &V Korea Co., Ltd., Seoul, Korea   ---

Signed and Sealed this

Twenty-fifth Day of September, 2001

Attest:

*Attesting Officer*

NICHOLAS P. GODICI
*Acting Director of the United States Patent and Trademark Office*